United States Patent
Nie et al.

(10) Patent No.: US 11,249,002 B2
(45) Date of Patent: Feb. 15, 2022

(54) MEASURING SIZE AND SHAPE OF PORE THROAT USING DIGITAL POROUS PLATE EXPERIMENTS

(71) Applicant: Halliburton Energy Services, Inc., Houston, TX (US)

(72) Inventors: Xiaobo Nie, Houston, TX (US); Jonas Toelke, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 215 days.

(21) Appl. No.: 16/656,213

(22) Filed: Oct. 17, 2019

(65) Prior Publication Data

US 2020/0309667 A1    Oct. 1, 2020

Related U.S. Application Data

(60) Provisional application No. 62/825,116, filed on Mar. 28, 2019.

(51) Int. Cl.
| | |
|---|---|
| *G01N 15/08* | (2006.01) |
| *E21B 49/08* | (2006.01) |
| *G01V 11/00* | (2006.01) |
| *G01N 33/24* | (2006.01) |
| *G01V 3/38* | (2006.01) |

(52) U.S. Cl.
CPC ......... *G01N 15/088* (2013.01); *E21B 49/087* (2013.01); *G01N 33/24* (2013.01); *G01V 3/38* (2013.01); *G01V 11/002* (2013.01)

(58) Field of Classification Search
CPC ......... G01N 15/088; G01N 33/24; G01V 3/38
See application file for complete search history.

(56) References Cited

U.S. PATENT DOCUMENTS

| | | |
|---|---|---|
| 6,453,727 B1 | 9/2002 | Lenormand et al. |
| 6,516,080 B1 | 2/2003 | Nur |
| (Continued) | | |

FOREIGN PATENT DOCUMENTS

| | | | |
|---|---|---|---|
| CN | 105427383 | | 4/2017 |
| CN | 107817199 B | * | 9/2019 |
| WO | 2016-137472 | | 9/2016 |

OTHER PUBLICATIONS

Moura et al. "Impact sample geometry on the measurement of pressure-saturation curves: Experiments and simulations," AGU Publications, pp. 8900-8926 (Year: 2015).*

(Continued)

*Primary Examiner* — John Fitzgerald
(74) *Attorney, Agent, or Firm* — John Wustenberg; C. Tumey Law Group PLLC

(57) ABSTRACT

A method may comprise obtaining a formation sample, scanning the formation sample to form a data packet, loading the data packet on an information handling machine, performing a digital porous plate experiment with the data packet, and determining geometry of a pore throat in the formation sample. A system may comprise a computer tomographic machine configured to scan a formation sample and create a data packet from the scan and an information handling system. The information handling system may be configured to configured to perform a digital porous plate experiment with the data packet and determine geometry of a pore throat in the formation sample.

20 Claims, 7 Drawing Sheets

(56) References Cited

U.S. PATENT DOCUMENTS

| | | | |
|---|---|---|---|
| 7,257,989 B2 | 8/2007 | Fleury | |
| 8,909,508 B2 | 12/2014 | Hurley et al. | |
| 9,285,301 B2 | 3/2016 | De Prisco et al. | |
| 9,575,203 B2* | 2/2017 | Chen | G01V 3/32 |
| 2012/0241149 A1* | 9/2012 | Chen | G01V 3/32 166/250.01 |
| 2012/0275658 A1* | 11/2012 | Hurley | G06T 7/11 382/109 |
| 2014/0019053 A1* | 1/2014 | de Prisco | E21B 49/00 702/12 |
| 2021/0116354 A1* | 4/2021 | Khodja | G01N 24/081 |

OTHER PUBLICATIONS

Lin et al., "Visualization and quantification of capillary drainage in the pore space of laminated sandstone by porous plate method using differential imaging X-ray microtography," AGU Publications, pp. 7457-7468 (Year: 2017).*

Silin, "Digital rock studies of tight porous media," Ernest Orlando Lawrence Berkeley National Laboratory (Year: 2012).*

Masalmeh et al., "Towards Predicting Multi-Phase Flow in Porous Media Using Digital Rock Physics: Workflow to Test the Predictive Capability of Pore-Scale Modeling," Society of Petroleum Engineers, SPE_177572-MS (Year: 2015).*

Hu et al. "Correlating Recovery Efficiency to Pore Throat Characteristics Using Digital Rock Analysis," Society of Petroleum Engineers, SPE-173393-MS (Year: 2015).*

Jerauld et al. "Validation of a Workflow for Digitally Measuring Relative Permeability," Society of Petroleum Engineers, SPE-188688-MS (Year: 2017).*

Sarker et al. "Application of Real Rock Pore-throat Statistics to Regular Pore Network Model" SPE 145751 (Year: 2011).*

Hu et al. "Correlating Recovery Efficiency to Pore Throat Characteristics Using Digital Rock Analysis" SPE 173393-MS (Year: 2015).*

International Search Report and Written Opinion for Application No. PCT/US2019/059281, dated Feb. 21, 2020.

De Prisco, G. et al., 'Computation of relative permeability functions in 3D digital rocks by a fractional flow approach using the lattice boltzmann method', International Symposium of the Society of Core Analysts, Aug. 27-30, 2012, pp. 1-12, Aberdeen, Scotland, UK, presentation SCA2012-36.

Raeesi, B. et al., 'Effect of surface roughness on wettability and displacement curvature in tubes of uniform cross-section', Colloids and Surfaces A: Physicochemical and Engineering Aspects, 2013, vol. 436, pp. 392-401.

Anovitz, L. M. et al., 'Characterization and analysis of porosity and pore structures', Reviews in Mineralogy & Geochemistry, 2015, vol. SO, pp. 61-164 the whole document.

Mason, G. et al., 'Effect of contact angle on the meniscus between two equal contacting rods and a plate', Journal of Colloid and Interface Science, Oct. 1983, vol. 95, No. 2, pp. 494-501 the whole document.

* cited by examiner

MEASURING SIZE AND SHAPE OF PORE THROAT USING DIGITAL POROUS PLATE EXPERIMENTS

BACKGROUND

This disclosure relates generally to systems and methods for analyzing rock samples or core samples taken from a formation. Specifically, identifying the properties and characteristic of one or more pores that may be attached to one another within the rock samples.

The size and shape of pore throat cross-sections are material parameters of reservoirs rock identified by a pore throat size and the shape of the pore throat. Currently, the pore throat cross-section combined with contact angle and surface roughness determines the capillary pressure of the wetting and non-wetting phase (oil, gas or water) invasion in drainage or imbibition. The capillary pressure as a function of invasion of non-wetting phase may be obtained by the mercury injection capillary pressure (MICP) experiment. However, the MICP cannot completely determine the pore size and shape.

BRIEF DESCRIPTION OF THE DRAWINGS

These drawings illustrate certain aspects of some examples of the present disclosure and should not be used to limit or define the disclosure.

DETAILED DESCRIPTION

This disclosure may generally relate to a system and method measuring the size and shape of pore throat cross-section using one or more digital capillary pressure experiments. For example, three-dimensional pore structures may be identified by a computer tomographic machine or other imaging technology. Then interfacial surfaces between wet and non-wet phases, such as water and oil, may be determined by one or more digital porous plate experiments. From the one or more digital porous plate experiments, a size and shape of the pore throat cross section may be found.

Figure 1:
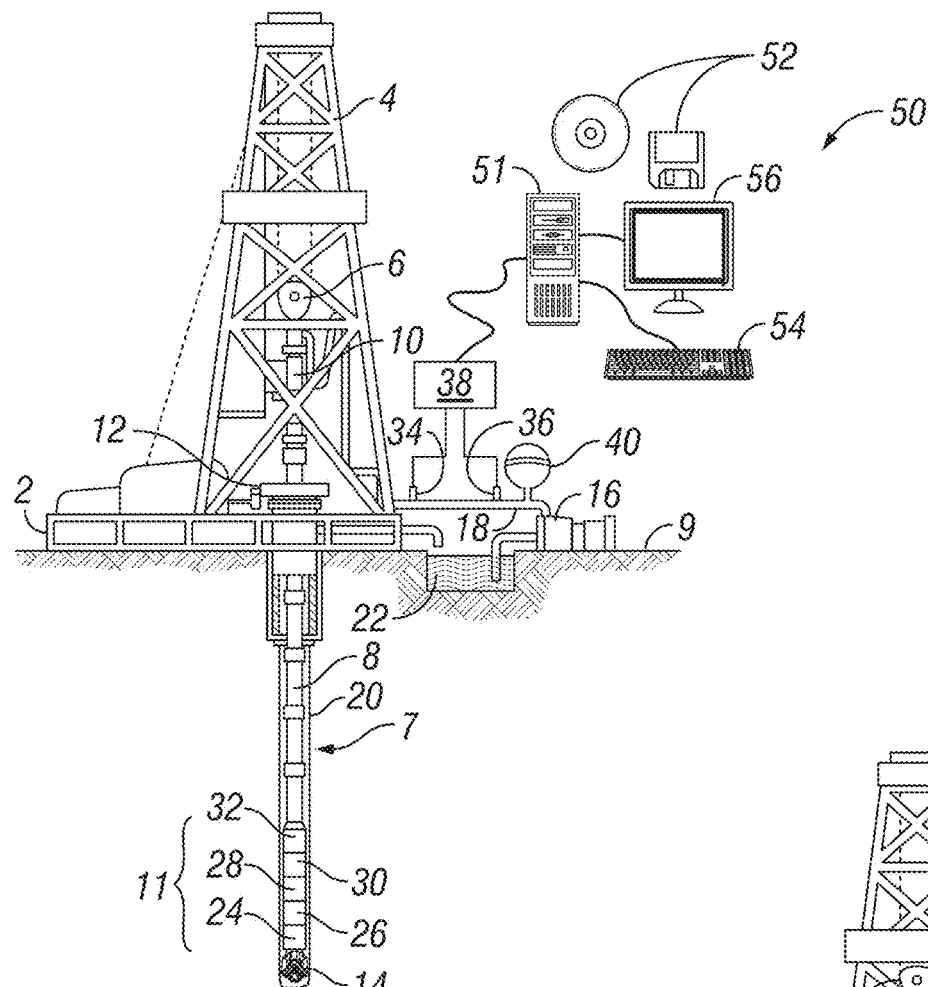
FIG. 1 shows an illustrative measuring-while-drilling (MWD) environment.

Accordingly, FIG. 1 shows an example illustration of a drilling operation. A drilling platform 2 is equipped with a derrick 4 that supports a hoist 6. Personnel may drill a borehole 7 for an oil or gas well using a drill string 8 of multiple concentric drill pipes. Hoist 6 suspends a top drive 10 that rotates drill string 8 as it lowers the drill string through wellhead 12. Connected to the lower end of drill string 8 is a drill bit 14. Drill bit 14 is rotated and drilling accomplished by rotating drill string 8, by use of a downhole motor near the drill bit, or by both methods. Recirculation equipment 16 pumps drilling fluid through supply pipe 18, through top drive 10, and down through drill string 8 at high pressures and volumes to emerge through nozzles or jets in drill bit 14. The drilling fluid then travels back up the hole via the annulus formed between the exterior of the drill string 8 and the borehole wall 20, through a blowout preventer, and into a retention pit 22 on the surface. On the surface, the drilling fluid is cleaned and then recirculated by recirculation equipment 16. The drilling fluid carries cuttings from the base of borehole 7 to surface 9 and balances the hydrostatic pressure in the rock formations.

A bottomhole assembly 11 (i.e., the lowermost part of drill string 8) includes thick-walled tubulars called drill collars, which add weight and rigidity to aid the drilling process. The thick walls of these drill collars make them useful for housing instrumentation and LWD sensors. Thus, for example, bottomhole assembly 11 of FIG. 1 may include position sensors, orientation sensors, pressure sensors, temperature sensors, vibration sensors, etc. From various bottomhole assembly sensors, the control and telemetry module 32 collects data regarding the formation properties and/or various drilling parameters and stores the data in internal memory. In addition, some or all of the data is transmitted to surface 9 by any suitable communication equipment. Without limitation, data transmission using mud pulse technology may be utilized.

Mud pulse technology may utilize a telemetry module 32, which modulates a resistance to drilling fluid flow to generate pressure pulses that propagate to the surface. One or more pressure transducers 34, 36 (isolated from the noise of the recirculation equipment 16 by a desurger 40) convert the pressure signal into electrical signal(s) for a signal digitizer 38. The signal digitizer 38 supplies a digital form of the pressure signals to an information handling system 50 or some other form of a data processing device. Information handling system 50 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 50 may be a processing unit 51, a network storage device, or any other suitable device and may vary in size, shape, performance, functionality, and price. Information handling system 50 may include random access memory (RAM), one or more processing resources such as a central processing unit (CPU) or hardware or software control logic, ROM, and/or other types of nonvolatile memory. Additional components of the information handling system 50 may include one or more disk drives, one or more network ports for communication with external devices as well as various input and output (I/O) devices, such as an input device 54 (e.g., keyboard, mouse, etc.) and a video display 56. Information handling system 50 may also include one or more buses operable to transmit communications between the various hardware components.

Alternatively, systems and methods of the present disclosure may be implemented, at least in part, with non-transitory computer-readable media 52. Non-transitory computer-readable media 52 may include any instrumentality or aggregation of instrumentalities that may retain data and/or instructions for a period of time. Non-transitory computer-readable media 52 may include, for example, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 2:
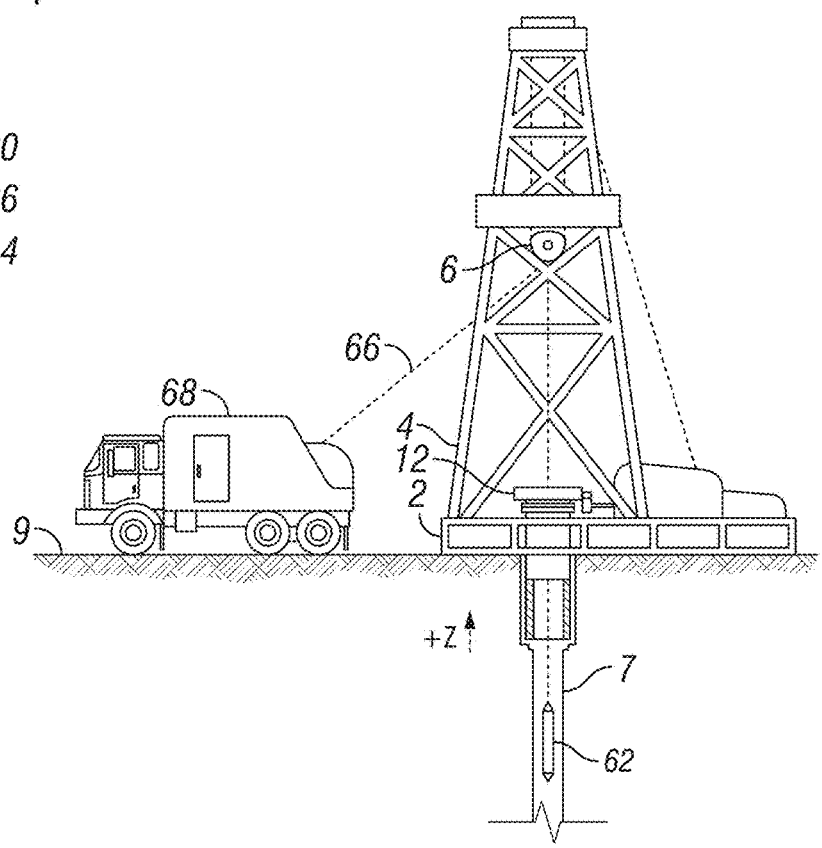
FIG. 2 shows an illustrative wireline coring environment.

With continued reference to FIG. 1, at various times during the drilling process, drill string 8 may be removed from the borehole 7. Referring to FIG. 2, once drill string 8 has been removed, coring operations may be conducted using a wireline tool 62, i.e., an instrument suspended by a cable 66 having conductors for transporting power to the tool and telemetry from wireline tool 62 to surface 9. Wireline tool 62 may include a sampling tool that may allow for wireline tool 62 to collect samples from a formation. Other formation property sensors may additionally or alternatively be included to measure formation properties as wireline tool 62 is pulled uphole. A logging facility 68 collects measurements from wireline tool 62 and includes one or more information handling systems 50 (e.g., referring to FIG. 1) for processing and storing the measurements gathered by wireline tool 62.

During drilling operations and/or measurement operations, samples of the geographical rock within a formation may be taken. For example, cuttings, as described above, may be circulated to the surface 9 in drilling fluid (e.g., referring to FIG. 1) and may be collected. Without limitation, wireline tool 62 may include tools and/or devices that may sample the formation during coring operations (e.g., referring to FIG. 2). These samples may be brought to surface 9 at the end of a coring operations. Samples of the formation may be analyzed on site and/or transported to an offsite location for further measurement operations.

Figure 3:
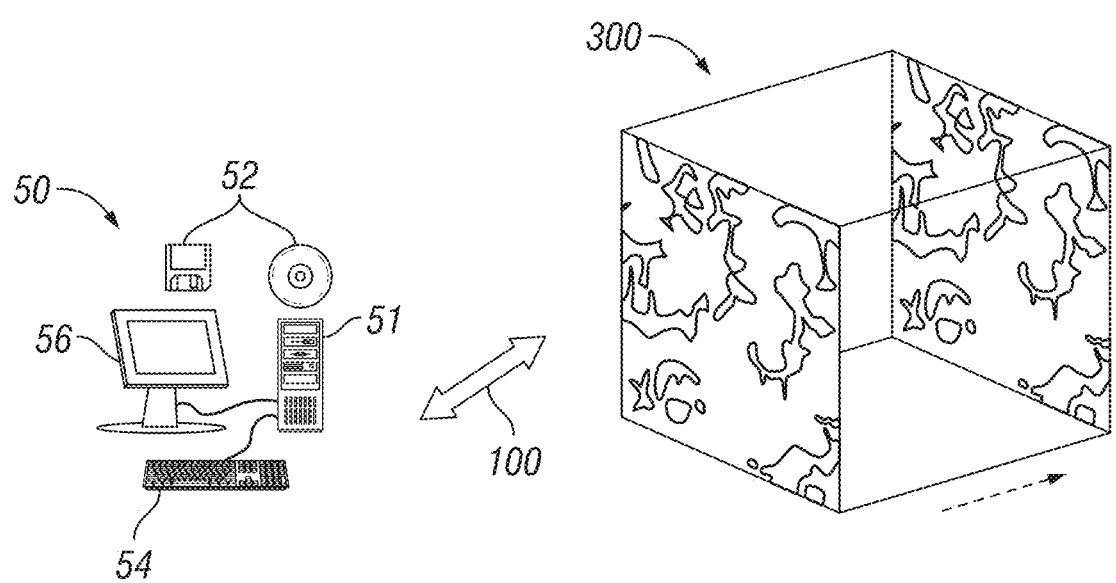
FIG. 3 illustrates an information handling machine attached to a scanning device.

Measurement operations may include the measurement of the size and shape of pore throat cross section using one or more digital porous plate experiments. A porous plate experiment is a measurement operation that may compute and display the phase saturation in a porous sample in dependence on the applied capillary pressure. As described above, a sample of the formation is recovered for analysis. Referring to FIG. 3, formation sample 300 may be scanned by a computer tomographic machine or other imaging technology to measure pore throat size and shape. Scanning formation sample 300 may produce data and/or a data packet that may be transferable to an information handling system 50. The data packet may be uploaded into an information handling system 50 through communications 100. It should be noted that communications 100 may be any suitable wired and/or wireless connections. The data packet may be shown on video display 56 for further review, analyses, and/or processing by personnel.

Figure 4A:
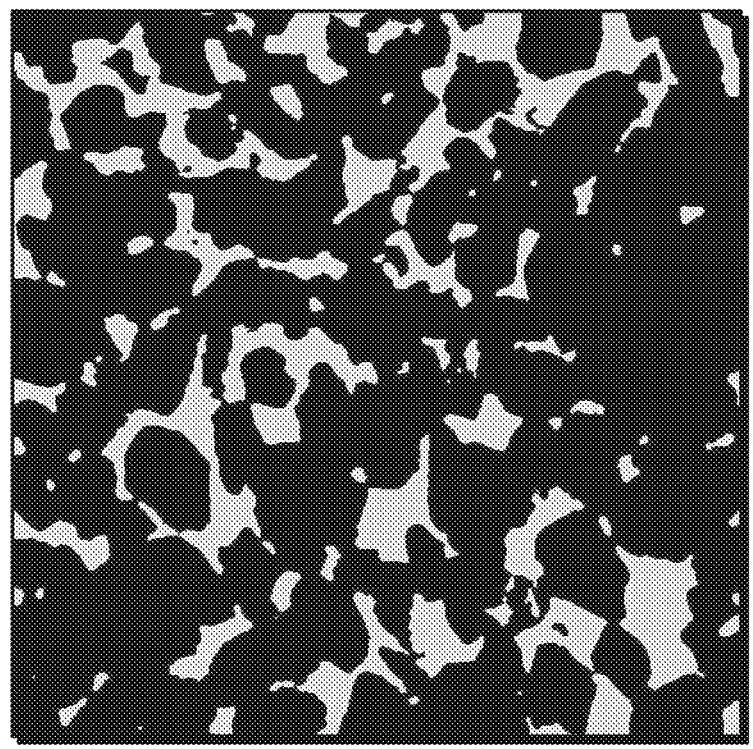
FIG. 4A illustrates a cross-sectional view of attached pores within a formation sample.
Figure 4B:
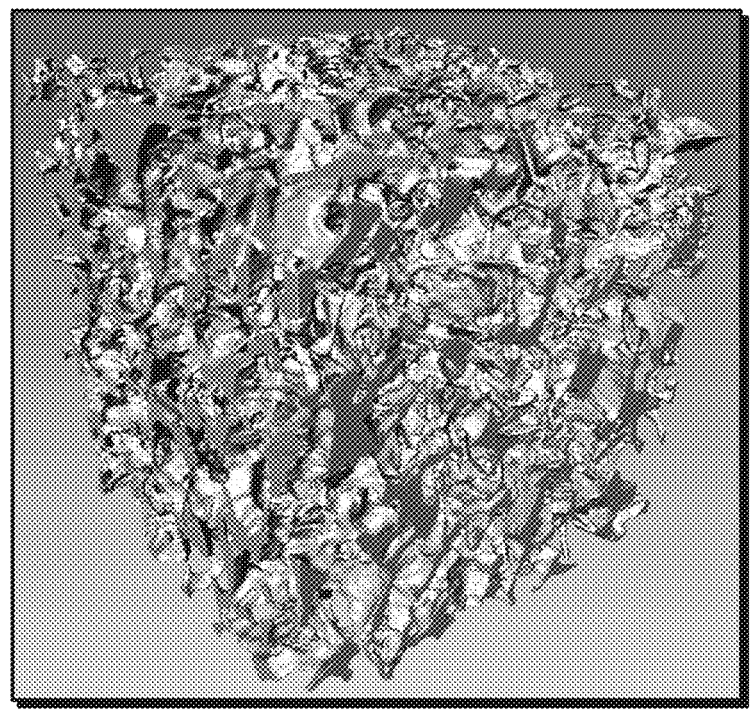
FIG. 4B illustrates a three-dimensional view of the formation sample.
Figure 5A:
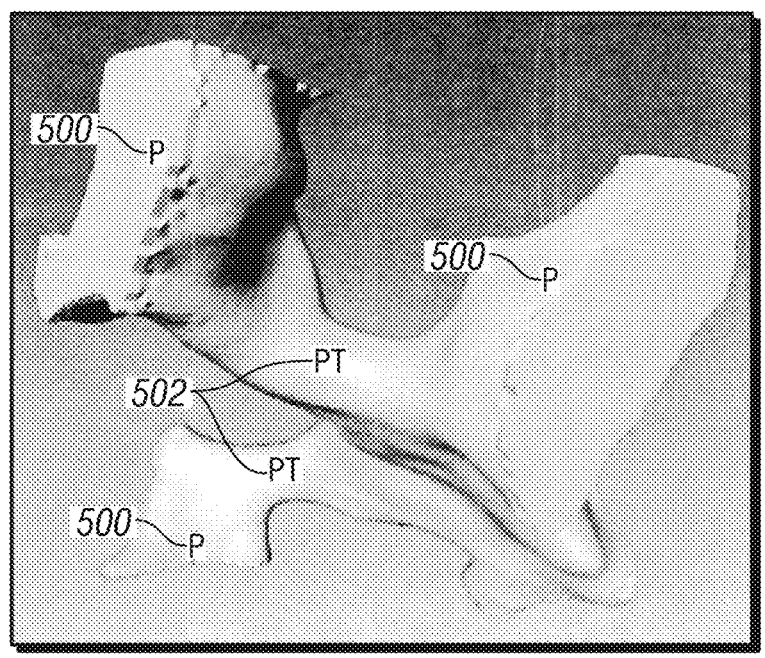
FIGS. 5A and 5B are a close-up view of pore in the three-dimensional view of the formation sample.
Figure 5B:
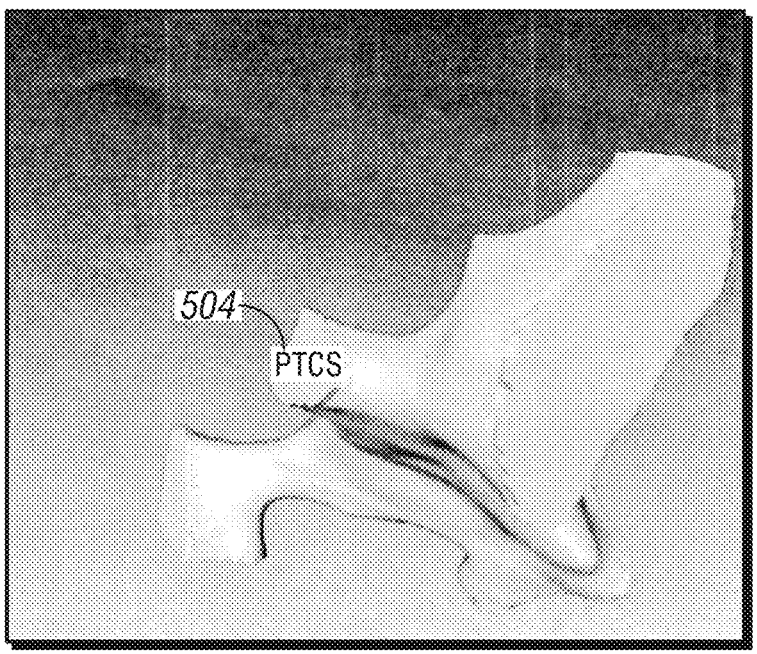

FIG. 4A is an example of a type of image shown on video display 56 that may represent the size and shape of a pore throat cross section from formation sample 300 (e.g., referring to FIG. 3). FIG. 4A is a two-dimensional representation of a cross section of formation sample 300. In examples, as illustrated in FIG. 4B, scanning of formation sample 300 may produce an interactive three-dimensional image that may resemble formation sample 300. The interactive model of FIG. 4B may allow for additional review of individual pores in a close-up view. For example, FIGS. 5A and 5B illustrate examples of a close-up image of one or more pore 500. FIG. 5A may additionally illustrate characteristics and properties of pore 500. As illustrated in FIG. 5A, one or more pores 500 may be connected to each other through a pore throat 502. FIG. 5B illustrates a throat cross section 504. Referring to both FIGS. 5A and 5B, pore 500 and pore throat 502 may provide material parameters that may allow for the determination of reservoir rock information. Pore throat cross section 504 may determine the capillary pressure of the non-wetting phase or wetting phase invasion during drainage or imbibition. The interface between the wetting and non-wetting phase may be known as a two-phase interface.

Figure 6:
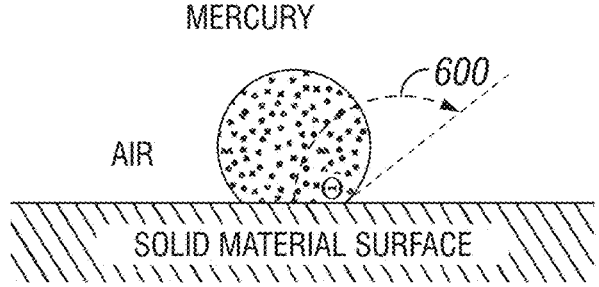
FIG. 6 illustrates a mercury droplet on a mineral surface.

In examples, capillary pressure as a function of invaded non-wetting phase may be obtained by a MICP experiment. The MICP experiment utilizes mercury for the measurement operations. Mercury is a liquid metal at ambient conditions that may behave as a non-wetting fluid when in contact with porous rock material. The movement of mercury in the porous rock material may be affected by the angles, slopes, shape, and/or the like within the porous rock material. For example, FIG. 6 illustrates an example illustration of contact angle 600 of mercury-air interface is in general between 130 and 140 degrees, for example, on solid mineral such as calcite quartz or others. The interfacial tension between air/mercury may have a value, for example, of 486.5 milliNewton/meter compared to air/water or oil/water or air/oil. These properties allow mercury to accurately perform capillary pressure experiments. Using mercury, the MICP experiment may be able to identify the distributions of pore throat size.

Figure 7:
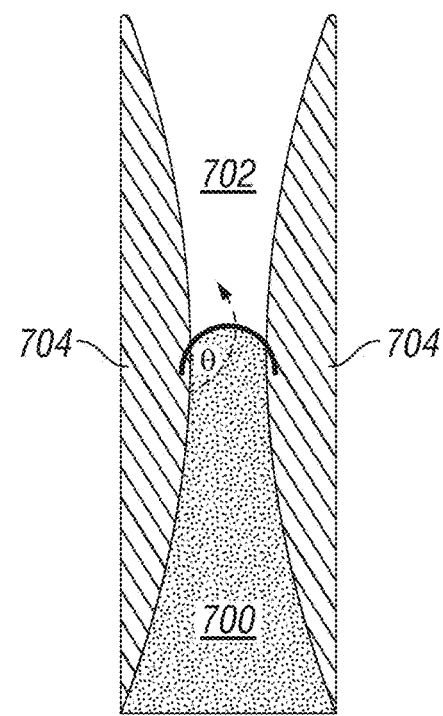
FIG. 7 mercury disposed in a pore during a MICP experiment.

FIG. 7 illustrates an example illustration of an MICP experiment with an inversion of mercury 700 into a dry pore space 702 of porous material 704. Pressure is applied to mercury 700 to push mercury 700 into dry pore space 702. To relate size of pore throat 502 (e.g., referring to FIG. 5) to capillary pressure, Equation (1) below, assuming the pore throat cross-section is a circle, is used:

$$Pc(Sw) = \frac{2\sigma\cos\theta}{r} \quad (1)$$

Here $P_c$ is capillary pressure, $\sigma$ is interfacial tension, $\theta$ is contact angle, r is radius of the pore throat, and Sw is the saturation in a volumetric sense of the wetting phase air. For example, $S_w$ may be expressed as:

$$S_w = \frac{V_{air}}{V_{pore}} \quad (2)$$

Where $V_{air}$ is the volume of air in the pore 500 (e.g., referring to FIG. 5). Equation 2 may assume a circular cross-section. If pore throat 502 includes a slit, the size of pore throat 502 may be determined by MICP experiments with an error of a factor of 2. A correct relationship is to use the two main radii of curvature (the pore throat section is approximated by an ellipse):

$$Pc(Sw) = \sigma\cos\theta\left(\frac{1}{r1} + \frac{1}{r2}\right) \quad (3)$$

Here $r_1$ and $r_2$ are the main radii of the interface between the wetting and non-wetting fluid in pore throat 502. These quantities are not available from a traditional physical MICP experiment. A digital MICP simulation, in a digital representation of the pore-structure of the rock, allows to quantify those values. Without limitation, the digital representation may allow for an accurate measurement of the properties in a wet phase and non-wet phase.

For example, fluid in a wet phase may tend to stay in corners or grooves of the rock surface. The presences of a wetting film and the stability of wet phase depend on the detail and shape of pore throat 502. Both of these properties may affect the resistivity index and wetting phase relative permeability. A digital representation of the pore-structure of the rock may allow for ascertaining these variables.

Using a digital representation, the size of pore throat 502 and shape have been measured using different geometrical operations with a computer tomographic machine or another image technology. Methods that use geometrical algorithms to divide the pore-space into pore bodies and throat are ambiguous. A more rigorous method is to compute the displacement of the wetting and non-wetting phase in the three-dimensional pore-space and to identify pore 500 and pore throats 502 as defined by the interfaces between wetting and non-wetting fluid.

The shape and structure of pores 500 may take any shape and form as shown in the examples of FIGS. 4A, 4B, 5A, and 5B. For example, pore throat 502 is a smaller channel which may connect two larger volumes, two pores 500 may be connected by two or more throats 502, and a narrow channel may have a fork and connect one or more pores 500. These properties may affect properties in a wetting phase and non-wetting phase.

Figure 8:
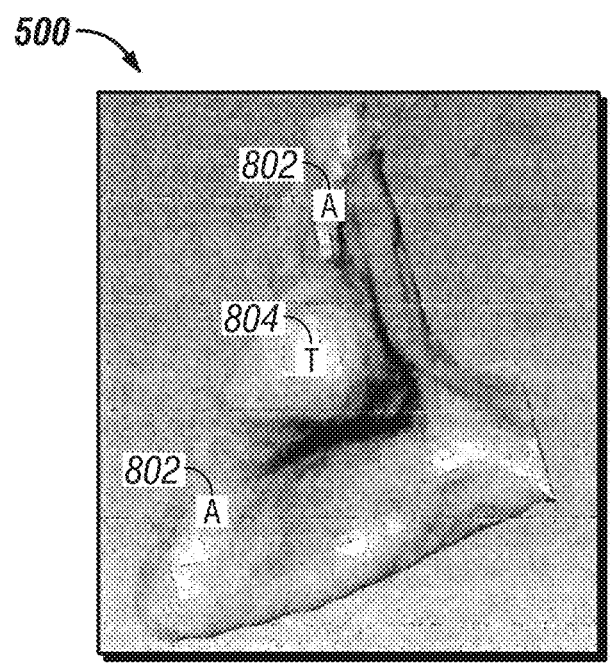
FIG. 8 illustrates a close-up view of an interface of non-wetting phase in the three-dimensional view of the formation sample.

Referring to FIG. 8 illustrates an example close-up view of an interface of non-wetting phase in pore 500. The three-dimensional pores are identified by image segmentation. The interface between wetting and non-wetting phases may be obtained using the non-wetting and wetting phase distribution at certain capillary pressure from a digital porous plate experiment.

Figure 9:
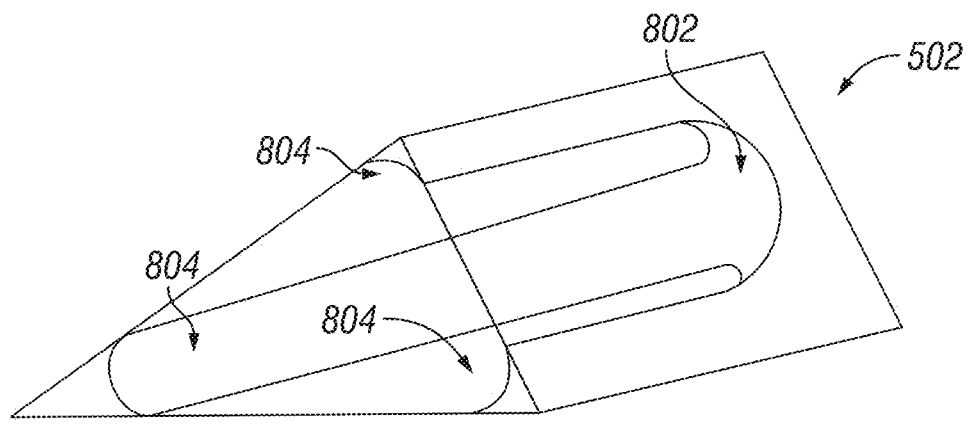
FIG. 9 illustrates a cross-section view of a pore throat with a terminal menisci and an arc menisci.

The interface between non-wetting and wetting phase may include three parts. The first part is the interface in the front of a pore throat and is called terminal meniscus 802. The second part is the interface located at the corner or crevice of pore 500 or pore throat 502 and is called arc meniscus 804. FIG. 9 illustrates another example of terminal meniscus 802 and arc meniscus 804. FIG. 9 illustrates a triangular cross-section of a pore throat 502 with terminal meniscus 802 and arc meniscus 804.

Referring back to FIG. 8, the first two parts of interface form a structure connecting arc meniscuses 804, which are narrow and long, to terminal meniscuses 802, which is round. The two curvatures of the interface are calculated and denoted as $c_1$ and $c_2$. It is assumed that $c_1$ is not larger than $c_2$. Furthermore, arc meniscus 804 is identified by a $c_1$ that is close to zero and terminal meniscus 802 is identified by the comparable $c_1$ and $c_2$ (i.e. $c_1$ and $c_2$ in the same order of magnitude).

Referring back to FIG. 3, during digital measurements, a volume from a formation sample 300 is used to perform a digital porous plate experiment. In the digital experiment, one side of the rock volume is attached to the reservoir of non-wet fluid through a porous plate that allows the non-wetting phase to pass through and block the wetting phase. The opposite side is attached to the reservoir of the wetting phase through a porous plate that allows the wetting phase to pass and block the non-wetting phase. The other four sides are blocked by solid walls. The non-wetting phase and wetting phase reservoirs have different uniform pressure values. The pressure difference between non-wetting phase (nw) and wetting phase (w) is the capillary pressure:

$$Pc = Pnw - Pw \quad (4)$$

where Pnw and Pw are non-wetting phase and wetting phase pressure, respectively. The capillary pressure increases slowly step by step. The non-wetting phase and wetting phase may enter or exit from the rock as the capillary pressure increases. The non-wetting phase and wetting phase distributions and saturations may change accordingly. The changes of non-wetting phase and wetting phase distributions are numerically simulated using any pore-scale simulator for immiscible two-phase Stokes flow. This includes lattice Boltzmann methods, finite difference, finite volume and finite element methods based on marker and cell, the volume of fluid method or phase field methods or combination thereof. Without limitation, the direct hydrodynamics pore flow method (DHD) or particle methods like smoothed particles hydrodynamics (SPH) may be used.

In FIG. 8, the interfaces between wet and non-wet phases, such as water and oil, are determined in the digital porous plate experiments. These interfaces are mainly located at front of different pore throats (i.e., terminal meniscus 802) for different capillary pressures. The two principal radii of the interfaces at the front of the throats are numerically calculated. The lengths of the major and minor axes are determined by the two principal radii and the contact angle used in the digital porous plate experiment. Some of these interfaces may be located at the corner of a pore throat (i.e., arc meniscus 804). The center of the pore throat is occupied by the non-wet phase and the wet phase stays in the corners or crevices. The interfacial shape (i.e. arc meniscus 804) and the shape of the wet phase fluid at the pore throat cross section may determine the corner shape of the pore throat. To include the effects of contact hysteresis, two or more digital porous plate experiments with different contact angles may be used. In the meantime, the contact angle hysteresis is also obtained.

Figure 10:
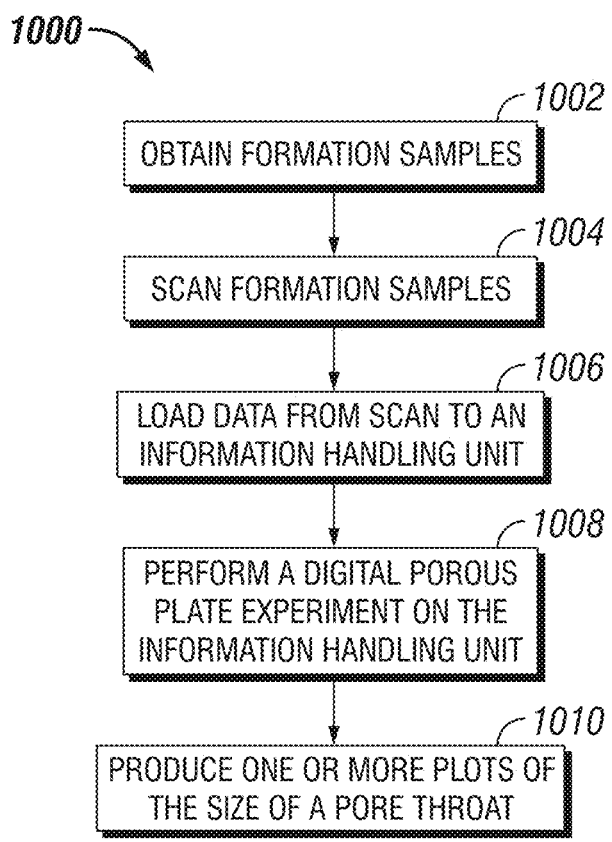
FIG. 10 shows a workflow for determining porosity in the formation sample.
Figure 11:
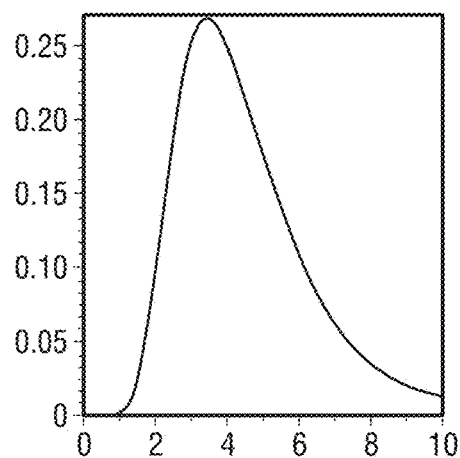
FIG. 11 illustrates a two-dimensional plot displaying a pore throat size.

FIG. 10 illustrates an example of flowchart 1000 for identifying porosity of a formation sample. In block 1002, a formation sample is obtained in drilling operations and/or coring operations, as described above in FIGS. 1 and 2. In block 1004, the formation sample is scanned by any suitable computer tomographic machine or another image technology. In block 1006, the data from the scans is loaded into an information handling system 50 (e.g., referring to FIG. 3) to form a data packet. In block 1008, one or more digital porous plate experiments are performed on information handling system 50 with the data packet. In block 1010 one or more plots may be produced to illustrate the size of pore throat 502 (e.g., referring to FIG. 5). For example, FIG. 11 illustrates current presentation of the size of pore throat 502. As illustrated in FIG. 11, the size of pore throat 502 found from an MCIP experiment may be illustrated as a plot with a horizontal axis related to the size of pore throat 502 and a vertical axis showing relative fraction of the volume of pore 500 (e.g., referring to FIG. 5) that may be filled with mercury.

Figure 12:
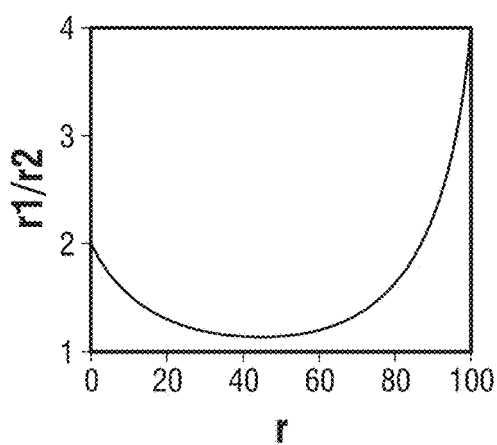
FIG. 12 illustrates a two-dimensional plot of a ratio of two pore throat radii.

FIG. 12 illustrates the ratio of the two pore throat radii gained by a digital MICP experiment. Here $r_1$ is the inverse of the first principal curvature and the axis labeled $r_2$ is the inverse of the second principal curvature. The $r_1$ and $r_2$ may be interpreted as a size of pore throat 502 (e.g., referring to FIG. 5). The x axis labeled $r_0$ is the averaged radius defined by:

$$\frac{2}{r0} = \frac{1}{r1} + \frac{1}{r2} \quad (5)$$

The variation of ratio of pore throat radius may be obtained as function of the averaged rams.

In examples, if pores 500 (e.g., referring to FIG. 5) may be slit-like the plot in FIG. 12 may show $r_1$ with a larger relative fraction than $r_2$. If the aperture of the cross-section is more compact, the relative fraction may be near and/or equal to $r_2$, which may be illustrated in circular or quadratic cross-section or a cross-section that may be close to an equilateral triangle.

Figure 13:
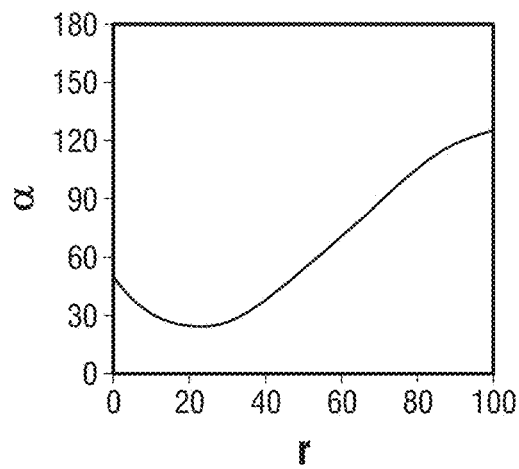
FIG. 13 illustrates a two-dimensional plot of a corner angle of a pore throat.

FIG. 13 illustrates the averaged corner angle of pore throat 502 (e.g., referring to FIG. 5) a gained by a digital MICP experiment as a function of the averaged radius $r_0$. Here α is the averaged corner angle of pore throats 502 with the same averaged pore throat 502 radius. The corner angle is 180 degree for a pore throat 502 with circular cross-section, is 90 degree for a rectangular cross-section, and is 60 degree for an equilateral triangle. The variation of the corner angle also may be obtained as a function the averaged radius.

As described above, a digital porous plate experiment may be more consistent than purely geometrical algorithms (that do not take into account fluid configurations) to measure the pore throat size and shape. Those purely geometrical algorithms are often connected to pore network modeling (PNM). As disclosed above, the digital porous plate experiment is based on the actual two-phase fluid configuration to determine the pore throat size and shape.

Statement 1. A method may comprise obtaining a formation sample, scanning the formation sample to form a data packet, loading the data packet on an information handling machine, performing a digital porous plate experiment with the data packet, and determining geometry of a pore throat in the formation sample.

Statement 2. The method of statement 1, further comprising identifying a two-phase interface for different capillary pressure.

Statement 3. The method of statements 1 or 2, further comprising extracting a terminal meniscus and arc meniscus.

Statement 4. The method of statement 3, further comprising calculating a curvature of the terminal meniscus.

Statement 5. The method of statement 3, further comprising calculating a curvature of the arc meniscus.

Statement 6. The method of statements 1-3, further comprising calculating one or more radii of the pore throat.

Statement 7. The method of statements 1-3 or 6, further comprising calculating one or more angles of a corner of the pore throat.

Statement 8. The method of statements 1-3, 6, or 7, further comprising calculating one or more angles of a groove of the pore throat.

Statement 9. The method of statements 1-3 or 6-8, further comprising forming a two-dimensional plot of a ratio of one or more radii from the digital porous plate experiment.

Statement 10. The method of statements 1-3 or 6-9, further comprising forming a two-dimensional plot of a corner angle of the pore throat.

Statement 11. A system may comprise a computer tomographic machine configured to scan a formation sample and create a data packet from the scan and an information handling system. The information handling system may be configured to perform a digital porous plate experiment with the data packet, and determine geometry of a pore throat in the formation sample.

Statement 12. The system of statement 11, wherein the information handling system is further configured to identify a two-phase interface for different capillary pressure.

Statement 13. The system of statements 11 or 12, wherein the information handling system is further configured to extract a terminal meniscus and arc meniscus.

Statement 14. The system of statement 13, wherein the information handling system is further configured to calculate a curvature of the terminal meniscus.

Statement 15. The system of statement 13, wherein the information handling system is further configured to calculate a curvature of the arc meniscus.

Statement 16. The system of statements 11-13, wherein the information handling system is further configured to calculate one or more radii of the pore throat.

Statement 17. The system of statements 11-13 or 16, wherein the information handling system is further configured to calculate one or more angles of a corner of the pore throat.

Statement 18. The system of statements 11-13, 16, or 17, wherein the information handling system is further configured to calculate one or more angles of a groove of the pore throat.

Statement 19. The system of statements 11-13, or 16-18, wherein the information handling system is further configured to form a two-dimensional plot of a ratio of one or more radii from the digital porous plate experiment.

Statement 20. The system of statements 11-13 or 16-19, wherein the information handling system is further configured to form a two-dimensional plot of a corner angle of the pore throat.

It should be understood that, although individual examples may be discussed herein, the present disclosure covers all combinations of the disclosed examples, including, without limitation, the different component combinations, method step combinations, and properties of the system.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method comprising:
   obtaining a formation sample;
   scanning the formation sample to form a data packet;
   loading the data packet on an information handling machine;
   performing a digital porous plate experiment with the data packet on the information handling machine; and
   determining geometry of a pore throat in the formation sample based on the digital porous plate experiment.

2. The method of claim 1, further comprising identifying a two-phase interface for different capillary pressure.

3. The method of claim 1, further comprising calculating one or more radii of the pore throat.

4. The method of claim 1, further comprising calculating one or more angles of a corner of the pore throat.

5. The method of claim 1, further comprising calculating one or more angles of a groove of the pore throat.

6. The method of claim 1, further comprising forming a two-dimensional plot of a ratio of one or more radii from the digital porous plate experiment.

7. The method of claim 1, further comprising forming a two-dimensional plot of a corner angle of the pore throat.

8. The method of claim 1, further comprising extracting a terminal meniscus and arc meniscus.

9. The method of claim 8, further comprising calculating a curvature of the terminal meniscus.

10. The method of claim 8, further comprising calculating a curvature of the arc meniscus.

11. A system comprising:
    a computer tomographic machine configured to scan a formation sample and create a data packet from the scan; and
    an information handling system configured to:
       perform a digital porous plate experiment with the data packet; and
       determine geometry of a pore throat in the formation sample based on the digital porous plate experiment.

12. The system of claim 11, wherein the information handling system is further configured to identify a two-phase interface for different capillary pressure.

13. The system of claim 11, wherein the information handling system is further configured to calculate one or more radii of the pore throat.

14. The system of claim 11, wherein the information handling system is further configured to calculate one or more angles of a corner of the pore throat.

15. The system of claim 11, wherein the information handling system is further configured to calculate one or more angles of a groove of the pore throat.

16. The system of claim 11, wherein the information handling system is further configured to form a two-dimensional plot of a ratio of one or more radii from the digital porous plate experiment.

17. The system of claim 11, wherein the information handling system is further configured to form a two-dimensional plot of a corner angle of the pore throat.

18. The system of claim 11, wherein the information handling system is further configured to extract a terminal meniscus and arc meniscus.

19. The system of claim 18, wherein the information handling system is further configured to calculate a curvature of the terminal meniscus.

20. The system of claim 18, wherein the information handling system is further configured to calculate a curvature of the arc meniscus.

\* \* \* \* \*

UNITED STATES PATENT AND TRADEMARK OFFICE
CERTIFICATE OF CORRECTION

PATENT NO. : 11,249,002 B2  
APPLICATION NO. : 16/656213  
DATED : February 15, 2022  
INVENTOR(S) : Xiaobo Nie and Jonas Toelke Page 1 of 1

It is certified that error appears in the above-identified patent and that said Letters Patent is hereby corrected as shown below:

In the Specification

Column 7, Line 13 delete "the averaged rams" and replace with --the averaged radius--.

Signed and Sealed this  
Fifth Day of April, 2022

Drew Hirshfeld  
*Performing the Functions and Duties of the*  
*Under Secretary of Commerce for Intellectual Property and*  
*Director of the United States Patent and Trademark Office*